June 10, 1941. I. E. SODERLUND Plant Pat. 474

APPLE

Filed July 20, 1939

Inventor
Ingermar Emil Soderlund
By Williamson & Williamson
Attorney

Patented June 10, 1941

Plant Pat. 474

UNITED STATES PATENT OFFICE

474

APPLE

Ingermar Emil Soderlund, Excelsior, Minn.

Application July 20, 1939, Serial No. 285,587

1 Claim. (Cl. 47—62)

The present invention relates to a new variety and strain of apple characterised particularly by its shape, color, taste and keeping qualities.

The mother tree which produced the present apple is located on my farm in the Lake Minnetonka region near Excelsior, Minnesota, and this tree was grown from a seed taken from a Northwestern Greening apple grown on my said farm, the seed having been selected by me with the end in view of developing a new variety of apple which would be extremely hardy, resistant to drought, of good size and color, and which would have excellent keeping qualities. I have asexually reproduced young trees from the original mother tree.

In the accompanying original drawing there is illustrated in color, an approximately average sized apple which is typical of the new variety developed by me. In the said drawing—

Figure 1:
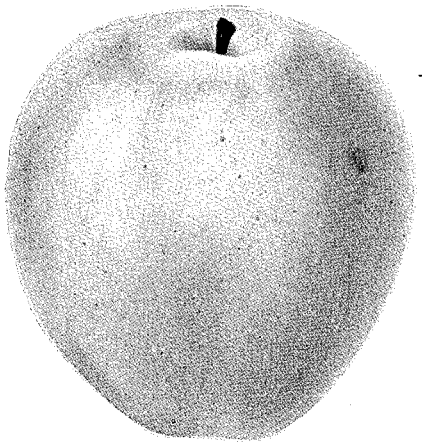
Fig. 1 is a perspective view looking chiefly toward the side of the apple but somewhat downwardly thereon.
Figure 2:
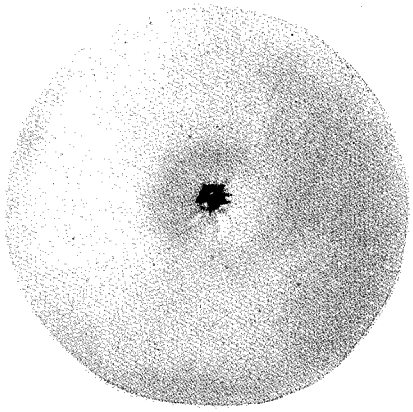
Fig. 2 is a bottom view looking at the basal end of the apple.
Figure 3:
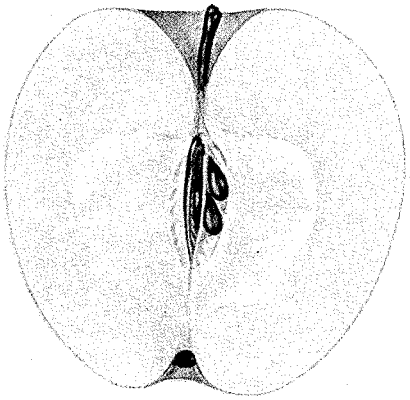
Fig. 3 is a sectional view taken vertically through the core of the apple.

I now refer more in detail to my new variety of fruit and to the tree bearing the same. The apple forming the subject matter of this application has the following peculiar characteristics which combine to distinguish it from other known varieties:

The apple is medium to large, many of the apples exceeding in size the particular apple illustrated, and the depth of the apple from top to bottom is somewhat greater relative to its diameter than is generally the case in most apples. The apple may be described as roundish conic in shape, the diameter of the apple at its lower end being considerably smaller than the diameter of the apple at its upper end and the basal portion of the apple having a greater taper than is generally found in most other apples. The apple is colored a bright attractive red ranging from nearly solid red to medium striped being red striped and splashed with a small amount of yellow ground color showing through the red. Even the reddest specimens do not lose the stripes entirely. Of course, the color of the apple varies somewhat depending on exposure to the sun, the ripening period and weather and soil conditions during growth. The apple has a gray scarf skin which is prominent around the basal end of the fruit and the skin carries large russet dots which slightly roughen the surface thereof. Each dot consists of a dark gray pin point superimposed on a yellow substantially circular background of greater diameter than the gray pin point. The skin is thin but tough. The stem of the apple is medium to long, set in a deep acute cavity.

The apple is particularly characterised by its fine keeping quality and delicious taste even after being held in storage for long periods of time. Apples held merely in common storage retain their fine flavor, juiciness, hardness, and other characteristics from the fall of the year until the following early summer without growing mealy or deteriorating, and the apple is, therefore, a fine winter keeper. The flesh is yellowish, tender but firm, medium fine grain, juicy mild sub-acid and moderately aromatic, and the quality is excellent. The apple when grown in the State of Minnesota is ready for use by November 15th.

The tree from which the apple is produced is characterised by its hardiness and its ability to stand heat and drought. It is easy to propagate by grafting and apparently bears early. The bark of the tree is a peculiar light grayish green color with small white dots and is smooth and somewhat on the order of a cherry tree for color. The leaves are on the order of those found on a Wealthy or Haralson apple tree. The branches are characterised by their strength to withstand wind and the weight of ripening fruit, and extend out from the trunk well, rising out of a big basin or collar. The tree maintains its central trunk and the branches are staggered relative to each other. The apples are spread quite evenly over the tree and do not grow in clusters. Apples do not drop off the tree but must be picked. The blossom is whitish pink.

As a convenient summary the following detailed description of this new variety of apple is given:

Tree: Medium in size. Vigorous. Spreading. Medium tall, dense. Round topped. Rapid growing. Hardy. Very productive. Regular bearer.

*Trunk.*—Stocky. Medium shaggy.

*Branches.*—Medium thick. Medium smooth. Reddish brown new growth changing to brownish gray green with age.

*Lenticels.*—Numerous. Conspicuous. Medium sized.

*Leaves.*—Length 2⅜ to 5″. Width 1¾ to 2⅜″. Medium sized. Narrow. Long. Oval to ovate. Taper pointed. Medium as to thickness. Medium green color. Slightly rugose. Lower surface slightly pubescent.

*Margin.*—Medium rounded serrate.

*Petiole.*—Length 1⅝ to 2¼″. Long slender. Color—cherry red in late season.

*Flowers.*—Date of bloom varies from season to season but is about the same as Northwestern Greening. Blooms late. Large size. Whitish pink a little pinker than Haralson or Wealthy.

Fruit: Date of ripening is late similar to Haralson and Northwestern Greening. Excellent winter keeper holding in common storage until May or later—ready for use by November 15th in Minnesota. Hangs well. Medium to large size averaging approximately 3″ in diameter—2⅜″ deep. Uniform. Roundish conic sometimes approaching ovate conic. Lower basal end of less diameter than upper stem end with more pronounced taper to lower end than usually found in other apples. Generally quite symmetrical sometimes slightly angular.

*Stem.*—Medium to long. Medium as to thickness.

*Cavity.*—Acute. Deep. Medium width. Well colored with faint greenish yellow rays. Symmetrical.

*Calyx.*—Tightly closed. Small.

*Lobes.*—Short. Medium broad.

*Basin.*—Medium in depth. Medium in width. Sometimes very slightly furrowed. Symmetrical.

*Skin.*—Thin but tough. Slightly roughened by conspicuous large russet dots evenly distributed over the surface, these dots consisting of grayish pin points on a yellow substantially circular background. Light bloom.

*Color.*—Bright attractive medium red; red striped and splashed with yellow ground color showing through the red, and the best colored specimens are nearly solid red but never entirely lose the stripe, characteristically overlaid with medium to heavy gray scarf skin.

*Dots.*—Numerous. Large. Russet. Areolar.

*Flesh.*—Yellowish. Firm. Tender. Medium fine grained, juicy, pleasantly mild subacid, moderately aromatic.

*Quality.*—Very good.

*Core.*—Medium sized. Closed. Carpels tufted.

*Core lines.*—Meeting.

*Calyx tube.*—Medium length. Medium width. Conic, stamens medium approaching basal.

*Seed.*—Large. Flat. Acuminate. Long medium brown.

*Use.*—An excellent dessert variety and equally good for culinary purposes.

The fruit above described and tree producing the same may vary in slight details depending on the climatic and soil conditions under which they are grown.

What is claimed is:

An apple variety substantially as herein shown and described, characterised by the fruit's excellent quality, roundish conic shape, bright medium red color, red striped and splashed on the surface of the apple with some yellow ground color showing through, thin but tough skin carrying russet dots distributed over the surface thereof, and yellowish, firm, tender, medium fine grained, juicy, pleasantly mild sub-acid flesh.

INGERMAR EMIL SODERLUND.